United States Patent
Li et al.

(10) Patent No.: US 8,395,768 B2
(45) Date of Patent: Mar. 12, 2013

(54) SCATTERING SPECTROSCOPY APPARATUS AND METHOD EMPLOYING A GUIDED MODE RESONANCE (GMR) GRATING

(75) Inventors: Zhiyong Li, Redwood City, CA (US); David A. Fattal, Mountain View, CA (US); Jingjing Li, Palo Alto, CA (US); R. Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 413 days.

(21) Appl. No.: 12/772,161

(22) Filed: Apr. 30, 2010

(65) Prior Publication Data

US 2011/0267611 A1   Nov. 3, 2011

(51) Int. Cl.
*G01J 3/44* (2006.01)
(52) U.S. Cl. ............... 356/301; 356/300; 356/445
(58) Field of Classification Search .......... 356/301, 356/300, 445
See application file for complete search history.

(56) References Cited

U.S. PATENT DOCUMENTS

| | | | |
|---|---|---|---|
| 5,216,680 A | 6/1993 | Magnusson et al. | |
| 5,598,300 A | 1/1997 | Magnusson et al. | |
| 7,167,615 B1 | 1/2007 | Wawro et al. | |
| 7,474,396 B2 | 1/2009 | Wu et al. | |
| 7,639,355 B2 | 12/2009 | Fattal et al. | |
| 7,869,032 B2* | 1/2011 | Zhang et al. | 356/317 |
| 8,111,401 B2* | 2/2012 | Magnusson et al. | 356/480 |
| 2006/0193550 A1 | 8/2006 | Wawro et al. | |
| 2009/0195879 A1 | 8/2009 | Dal Negro et al. | |
| 2009/0248367 A1 | 10/2009 | Naya et al. | |
| 2011/0181946 A1* | 7/2011 | Magnusson et al. | 359/346 |

OTHER PUBLICATIONS

Anne-Laure Fehrenbach et al, "Experimental demonstration of a narrowband, angular tolerant, polarization independent, doubly periodic resonant grating filter," Optics Letters, vol. 32, No. 15, Aug. 1, 2007, pp. 2269-2271.

Song Peng and G. Michael Morris, "Resonant scattering from two-dimensional gratings," J. Opt. Soc. Am. A, vol. 13, No. 5, May 1996, pp. 993-1006.

David Rosenblatt et al., "Resonant Grating Waveguide Structures," IEEE J. Quantum Electronics, vol. 33, No. 11, Nov. 1997, pp. 2038-2059.

Jingjing Li et al., "Plasnnonic optical antennas on dielectric gratings with high field enhancement for surface enhanced Raman spectroscopy," Applied Physics Letters, vol. 94, 2009, 263114-1 to 263114-1.

* cited by examiner

*Primary Examiner* — Layla Lauchman (57) ABSTRACT

A scattering spectroscopy apparatus, system and method employ guided mode resonance (GMR) and a GMR grating. The apparatus includes a GMR grating having a subwavelength grating, and an optical detector configured to receive a portion of a scattered signal produced by an interaction between an excitation signal and an analyte associated with a surface of the GMR grating. A propagation direction of the received portion of the scattered signal is substantially different from a propagation direction of a GMR-coupled portion of the excitation signal within the GMR grating. The system includes the apparatus and an optical source. The method includes exciting a GMR in a GMR grating, interacting a GMR-coupled portion of the excitation signal with an analyte to produce a scattered signal and detecting a portion of the scattered signal.

20 Claims, 4 Drawing Sheets

SCATTERING SPECTROSCOPY APPARATUS AND METHOD EMPLOYING A GUIDED MODE RESONANCE (GMR) GRATING

STATEMENT REGARDING FEDERALLY SPONSORED RESEARCH OR DEVELOPMENT

This invention has been made with government support under Contract No. HR0011-09-3-0002, awarded by Defense Advanced Research Projects Agency. The government has certain rights in the invention.

CROSS-REFERENCE TO RELATED APPLICATIONS

N/A

BACKGROUND

Scattering spectroscopy is an important means of identifying, monitoring and characterizing a variety of analyte species (i.e., analytes) ranging from relatively simple inorganic chemical compounds to complex biological molecules. Among the various types of scattering spectroscopy are methodologies that exploit Raman scattering and scattering due to fluorescence (e.g., fluorescence scattering) from an analyte. In general, scattering spectroscopy employs a signal to excite the analyte that, in turn, produces a response or scattered signal that is dependent on a characteristic (e.g., constituent elements of) the analyte. By detecting and analyzing the scattered signal (e.g., using spectral analysis), the analyte may be identified and even quantified, in some instances.

Unfortunately, the scattered signal may be very weak in many instances. For example, a response or scattered signal produced by Raman scattering may be many orders of magnitude smaller than the excitation signal used to elicit the production of the Raman scattering signal. As a result, detecting the scattered signal in the presence of the excitation signal may represent a significant challenge.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which.

Certain embodiments of the present invention have other features that are one of in addition to and in lieu of the features illustrated in the above-referenced figures. These and other features of the invention are detailed below with reference to the preceding drawings.

DETAILED DESCRIPTION

Embodiments of the present invention facilitate scattering spectroscopy of an analyte by enhancing an excitation field and spatially filtering a scattered signal produced by excitation of the analyte. In particular, a field (i.e., an electromagnetic field) of an excitation signal is enhanced by a guided mode resonance. In turn, the enhanced field interacts with or excites the analyte to produce a stronger scattered signal than would have been produced by the excitation signal alone in the absence of the guided mode resonance. In addition, embodiments of the present invention facilitate scattering spectroscopy by providing spatial filtering of the scattered signal. In particular, according to various embodiments, the scattered signal may be separated from portions of the excitation signal by a differential direction of propagation. Hence, not only is the strength of the scattered signal enhanced by the guided mode resonance but detection of the scattered field may be facilitated by the spatial filtering, according to the embodiments of the present invention. The scattering spectroscopy of the present invention may include, but is not limited to, Raman spectroscopy (e.g., surface enhanced Raman spectroscopy or SERS) and fluorescence spectroscopy.

As used herein, a 'guided-mode resonance' is defined as an anomalous resonance excited in, and simultaneously extracted from, a waveguide by a phase-matching element such as a diffraction grating. An excitation signal or wave (e.g., light) incident on the diffraction grating is coupled into and is essentially, but generally temporarily, 'trapped' as energy in a resonance mode in the waveguide under some circumstances, such as certain combinations of angle of incidence and signal wavelength. The resonance mode may manifest as an excitation of surface waves on a surface of a metallic grating or as a resonant wave (e.g., guided-mode or quasi guided-mode) within a body of a dielectric layer of the waveguide (e.g., as exemplified by various embodiments of the present invention), for example. Specifically, the resonance mode or energy that is trapped within the dielectric layer of the waveguide is referred to by definition herein as a guided mode resonance coupled (GMR-coupled) signal or portion of a signal. The trapped energy may subsequently escape from the waveguide and combine one or both of constructively and destructively with either a signal reflected by the grating or a signal transmitted through the grating. Guided-mode resonances are also often referred to as 'leaky resonances'.

A 'guided-mode resonance (GMR) grating' herein is defined as any diffraction grating coupled with a waveguide that can support a guided-mode resonance. Conventional GMR gratings are also known and referred to as 'resonant grating waveguides' and 'dielectric waveguide gratings'. For example, an optical GMR grating may comprise a dielectric slab waveguide with a diffraction grating, or simply a 'grating,' formed in or on a surface layer thereof. The diffraction grating may comprise grooves or ridges formed on a surface of the dielectric slab. In another example, the GMR grating is a planar dielectric sheet having a periodically alternating refractive index (e.g., phase grating) within the dielectric sheet. An exemplary phase grating may be formed by forming a periodic array of holes in and through the dielectric sheet. A signal incident on the surface of a GMR grating that excites a guided-mode resonance therein may be simultaneously extracted as one or both of a reflected signal (i.e., reflected waves) that reflects from an incident surface of the GMR grating and a transmitted signal (i.e., transmitted waves) that passes through the GMR grating and out a side of the GMR grating that is opposite the incident surface.

In various embodiments, the GMR grating may comprise either a one dimensional (1-D) grating or a two dimensional (2-D) grating. A 1-D grating may comprise a set of parallel and essentially straight grooves that are periodic only in a first direction (e.g., along an x-axis), for example. An example of a 2-D grating comprises an array of holes in a dielectric slab or sheet where the holes are periodically spaced along two orthogonal directions (e.g., along both an x-axis and a y-axis). A further discussion of GMR gratings and guided-mode resonance that applies to the GMR grating of the present invention may be found, for example, in Magnusson et al., U.S. Pat. No. 5,216,680 and Wawro et al., U.S. Pat. No. 7,167,615, both of which are incorporated by reference in their entirety herein.

In various embodiments, a scattering spectroscopy apparatus or system employing a GMR grating according to the present invention may be integrated onto or into essentially any surface and generally utilizes a relatively small form factor or foot print on the surface. In particular, the spectroscopy apparatus or system may be fabricated using many conventional manufacturing methodologies including, but not limited to, one or both of microlithography-based surface patterning and nanolithography-based surface patterning, used in circuit fabrication. For example, conventional semiconductor manufacturing techniques (e.g., a CMOS compatible fabrication process) may be employed to create a GMR grating on or in a surface of a photonic integrated circuit (IC). As such, a scattering spectroscopy apparatus or system employing the GMR grating of the various embodiments of the present invention may be readily integrated with conventional photonic elements and circuitry on an IC. Moreover, such an exemplary IC-based scattering spectroscopy apparatus or system may be realized within a surface footprint as small as one square millimeter (mm) or less, for example, using currently available manufacturing methods.

By definition herein, 'nanoscale' means a dimension that is generally less than about 1000 nanometers (nm). For example, a structure that is about 5-100 nm in extent is considered a nanoscale structure.

For simplicity herein, no distinction is made between a substrate or slab and any layer or structure on the substrate/slab unless such a distinction is necessary for proper understanding. Likewise, all gratings (i.e., diffraction gratings) are referred to generically unless a distinction is necessary for proper understanding. Further, as used herein, the article 'a' is intended to have its ordinary meaning in the patent arts, namely 'one or more'. For example, 'a layer' generally means one or more layers and as such, 'the layer' means 'the layer(s)' herein. Also, any reference herein to 'top', 'bottom', 'upper', 'lower', 'up', 'down', 'left' or 'right' is not intended to be a limitation herein. Herein, the term 'about' when applied to a value generally means plus or minus 10% unless otherwise expressly specified. Moreover, examples herein are intended to be illustrative only and are presented for discussion purposes and not by way of limitation.

Figure 1A:
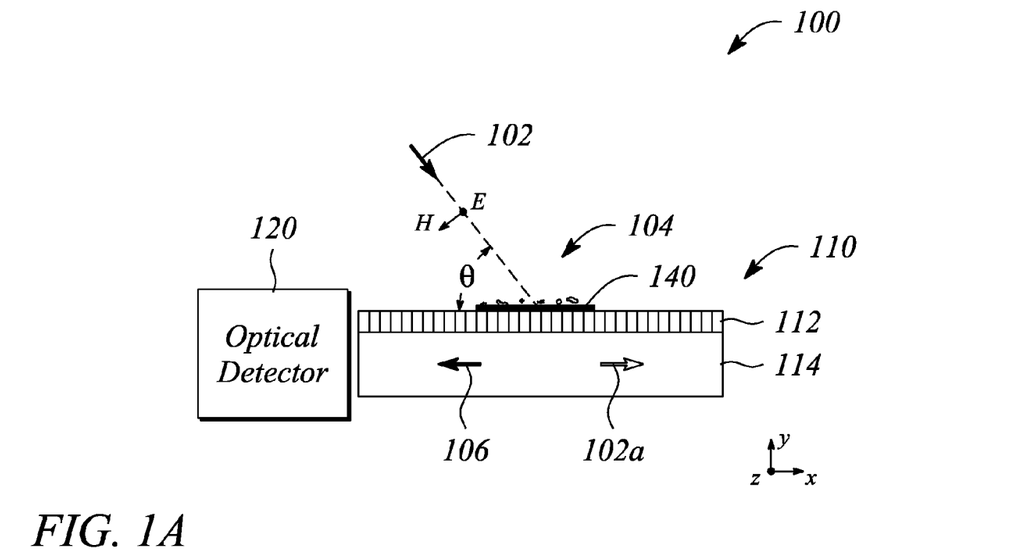
FIG. 1A illustrates a cross sectional view of a scattering spectroscopy apparatus, according to an embodiment of the present invention.
Figure 1B:
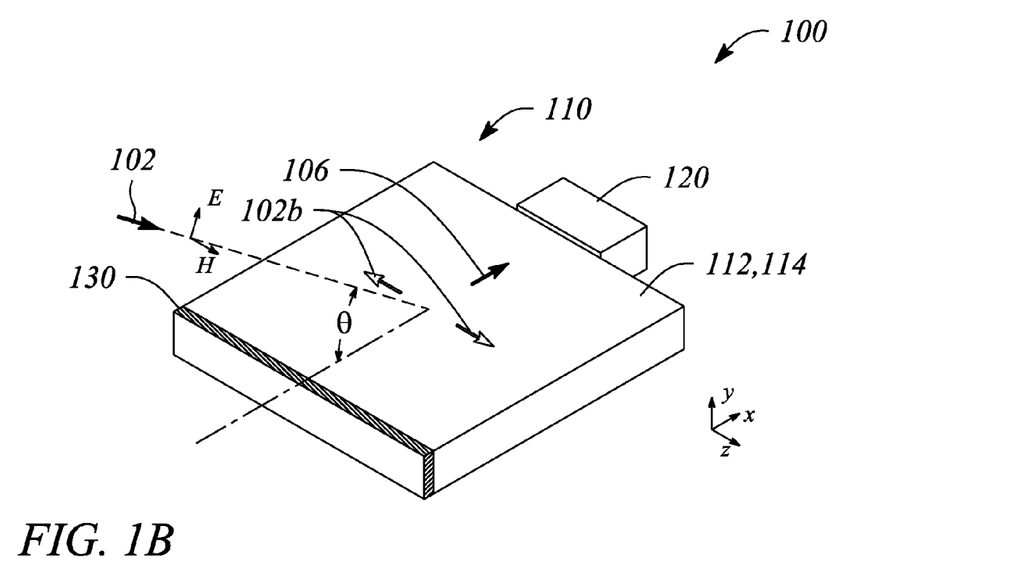
FIG. 1B illustrates a perspective view of a scattering spectroscopy apparatus, according to another embodiment.

FIG. 1A illustrates a cross sectional view of a scattering spectroscopy apparatus 100, according to an embodiment of the present invention. FIG. 1B illustrates a perspective view of a scattering spectroscopy apparatus 100, according to another embodiment. As illustrated, the scattering spectroscopy apparatus 100 receives an excitation signal 102. The excitation signal 102 may be an optical signal produced by a laser, according to some embodiments. The excitation signal 102 has an oblique angle of incidence θ. In particular, the angle of incidence θ is equal to or greater than zero degrees and less than about 90 degrees, according to some embodiments. In some embodiments, the excitation signal has a transverse electric (TE) polarization. In some other embodiments, a polarization of the excitation signal 102 is transverse magnetic (TM).

In various embodiments, the excitation signal 102 interacts with an analyte 104 to produce a scattered signal 106. In some embodiments, the scattered signal 106 comprises a signal resulting from Raman scattering (i.e., a Raman scattering signal) including one or both of Stokes scattering and anti-Stokes scattering. In such embodiments, the scattering spectroscopy apparatus 100 may be used to perform surface enhanced Raman spectroscopy (SERS), for example. In another example, the scattering spectroscopy apparatus 100 may be employed to perform fluorescence spectroscopy. In other embodiments, the scattering signal 106 may comprise a signal produced by Rayleigh scattering.

The scattering spectroscopy apparatus 100 comprises a guided mode resonance (GMR) grating 110. By definition herein, the GMR grating comprises a grating 112 (i.e., a diffraction grating) adjacent to a dielectric slab waveguide 114. In particular, in some embodiments, the grating 112 adjacent to the dielectric slab waveguide 114 is largely confined to a surface (e.g., a top surface) of the dielectric slab waveguide 114 and does not extend into the dielectric slab waveguide 114 to an appreciable extent. For example, the grating 112 may be mechanically formed into a material of the top surface of the dielectric slab waveguide 114. In another example, the grating 112 is formed one or both of from and into a material layer on the top surface of the dielectric slab waveguide 114. In other embodiments, being adjacent to the dielectric slab waveguide 114 means that the grating 112 may extend into or be partially coextensive with the dielectric slab waveguide 114. In yet other embodiments, the grating 112 and adjacent dielectric slab waveguide 114 are largely or even entirely coextensive (see for example FIG. 2B, described below).

In various embodiments, the grating 112 comprises a periodic array of grating elements. The periodic array is characterized by a grating pitch or period Λ (i.e., spacing between elements). In some embodiments, the grating 112 has a subwavelength grating period Λ. By 'subwavelength' it is meant that the grating period Λ is less than about a wavelength of the excitation signal 102. In such embodiments, the GMR grating 110 is said to have a 'subwavelength grating.'

In some embodiments, the GMR grating 110 comprises a one-dimensional (1-D) grating 112. Such embodiments are termed a '1-D GMR grating' herein. The 1-D grating 112 is characterized by a 1-D periodic array of grating elements having a grating period Λ. In some embodiments, the 1-D periodic array is singly periodic and is characterized by a single grating period Λ. In other embodiments, the 1-D periodic array may have more than one grating period Λ. For example, the 1-D periodic array may be doubly periodic. In another example, there may be three or more grating periods Λ.

Figure 2A:
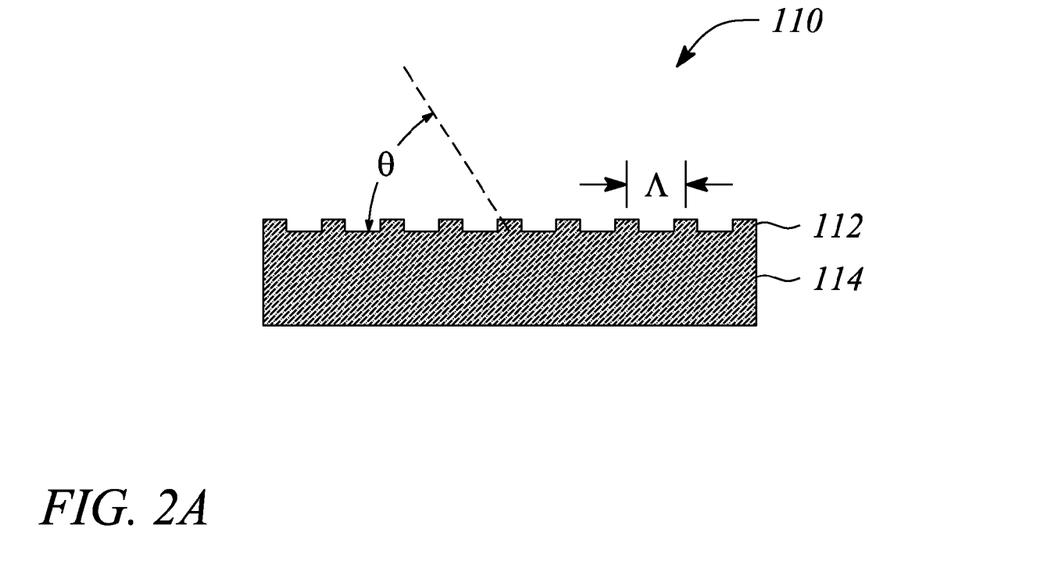
FIG. 2A illustrates a cross sectional view of a 1-D GMR grating, according to an embodiment of the present invention.

FIG. 2A illustrates a cross sectional view of a 1-D GMR grating 110, according to an embodiment of the present invention. As illustrated, the 1-D GMR grating 110 has a 1-D grating comprising a 1-D surface profile of surface features formed into and onto the top surface of the dielectric slab waveguide 114. For example, the surface features may be one or both of substantially parallel ridges and substantially parallel grooves spaced apart from one another by the grating period Λ. The 1-D surface profile comprising the surface features may be formed mechanically by molding or etching the top surface of the dielectric slab waveguide 114, for example. In another example, the 1-D surface profile illustrated in FIG. 2A may be produced by depositing and optionally patterning another material (e.g., a dielectric or a metal) on the top surface of the dielectric slab waveguide 114.

Figure 2B:
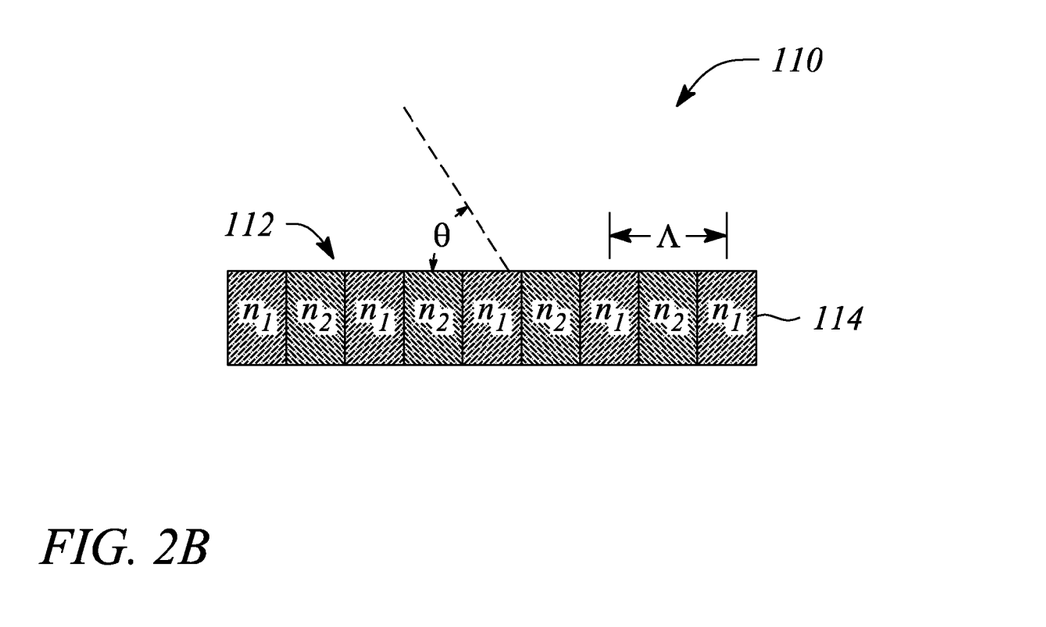
FIG. 2B illustrates a cross section of a 1-D GMR grating, according to another embodiment of the present invention.

FIG. 2B illustrates a cross section of a 1-D GMR grating 110, according to another embodiment of the present invention. As illustrated in FIG. 2B, the grating 112 of the 1-D GMR grating 110 comprises a periodic array of dielectric features. Herein and by way of definition, a 'dielectric feature' is characterized by a change in a refractive index $n_A$ of a material A of the dielectric feature relative to a refractive index $n_B$ of a material B (e.g., a different dielectric feature) that is adjacent to or that adjoins the dielectric feature. In various embodiments, the dielectric features may be formed one or both of adjacent to a surface of the dielectric slab waveguide 114 and within the dielectric slab waveguide 114 itself.

In particular, as illustrated in FIG. 2B, the 1-D periodic array of dielectric features comprises periodically alternating strips of a first dielectric material and a second dielectric material within the dielectric slab waveguide 114. The strips are periodically spaced apart at the grating period Λ and are substantially parallel to one another, as illustrated. In some embodiments, a width measured in a direction of the grating period Λ (i.e., in a direction of alternation of the strips or orthogonal to the strips) is essentially the same from one strip to the next. A refractive index $n_1$ of the first dielectric material differs from a refractive index $n_2$ of the second dielectric material, which results in a periodically alternating refractive index along the direction of the grating period Λ. Hence, the 1-D grating of FIG. 2B comprises a periodic array of dielectric features adjacent to the top surface of the dielectric slab waveguide 114. Further as illustrated, the periodically alternating refractive indices that produce the grating 112 are substantially within the dielectric slab waveguide 114. As such, the embodiment illustrated in FIG. 2B is an example of the grating 112 and dielectric slab waveguide 114 being substantially coextensive.

In other embodiments (not illustrated), the alternating dielectric features (e.g., the strips) formed into dielectric slab waveguide 114 that comprise the grating 112 may be localized at or in a vicinity of the surface such that a portion, and in some embodiments a substantial portion, of the dielectric slab waveguide 114 extends below the grating 112. In yet other embodiments (not illustrated), the grating 112 may comprise a periodic array of both surface features and dielectric features. In yet other embodiments, the array of surface features may comprise dielectric features.

In other embodiments, the GMR grating 110 comprises a two-dimensional (2-D) grating 112 and is referred to herein as a 2-D GMR grating 110. The 2-D grating 112 comprises a 2-D periodic array of grating elements. The grating elements may comprise one or both of surface features and dielectric features, according to various embodiments. In some embodiments, the grating elements comprise surface features on a surface (e.g., a top surface) of the dielectric slab waveguide. In some embodiments, the grating elements comprise surface features formed in the surface. In some embodiments, the grating elements comprise dielectric features one or more of on the surface, within a surface and within the dielectric slab waveguide itself.

Figure 3:
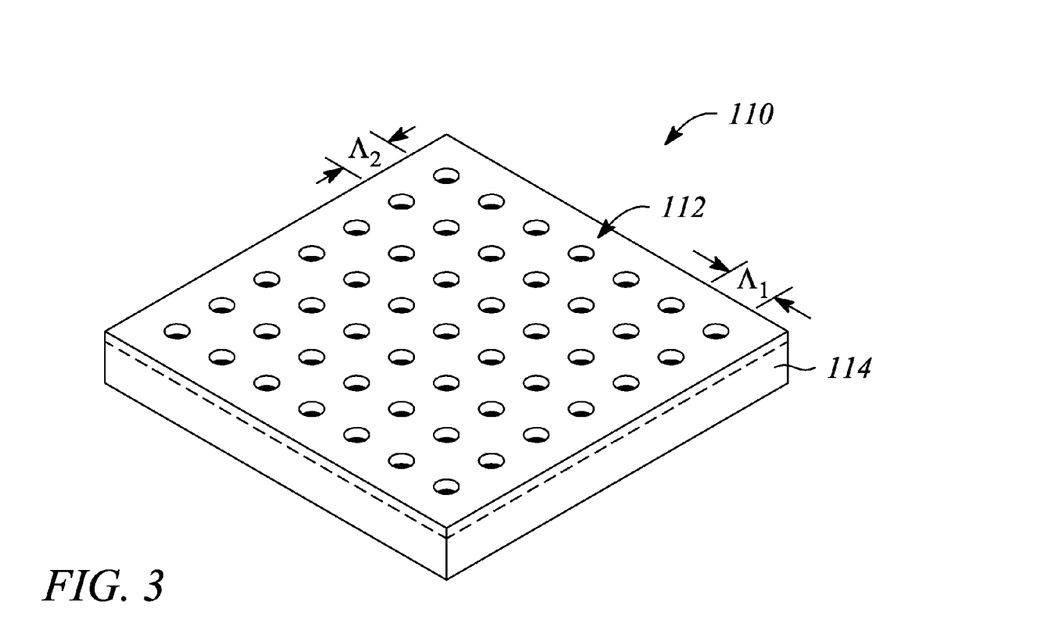
FIG. 3 illustrates a perspective view of a 2-D GMR grating, according to an embodiment of the present invention.

FIG. 3 illustrates a perspective view of a 2-D GMR grating 110, according to an embodiment of the present invention. As illustrated, the grating 112 of the 2-D GMR grating 110 comprises a 2-D periodic array of holes in a surface layer of the dielectric slab 114. The 2-D periodic array of holes has a 2-dimensional period Λ that introduces a periodically repeating refractive index discontinuity in the surface layer of the dielectric slab waveguide 114. The periodically repeating refractive index discontinuity produces the grating 112.

For example, the dielectric slab waveguide 114 may comprises a silicon on insulator (SOI) wafer and the grating 112 may comprise a square lattice of holes etched in a surface of the silicon (Si). In this example, the holes may have a diameter of about 400 nm and be etched to a depth of about 25 nm. A spacing between, or period Λ of, the holes in the square lattice may be about 1.05 micron (µm) (i.e., where $Λ=Λ_1=Λ_2$). In this example, the Si may be a layer having a thickness of about 50 nm.

While illustrated in FIG. 3 as holes, the 2-D grating 112 may be produced by essentially any means for introducing a 2-D periodically repeating discontinuity. For example, the holes described above may be filled with a dielectric material of a different refractive index than that of the dielectric slab 114. The filled holes may be viewed equivalently as dielectric features while the un-filled holes may be considered surface features. In another example, the 2-D grating is provided by holes or filled holes (e.g., dielectric plugs) that extend completely through an entire thickness of the dielectric slab 114. In yet another example, an array of protruding surface features (e.g., bumps) may be employed as the 2-D grating. In some embodiments, a grating period $Λ_1$ of the 2D diffraction grating 112 may be different in a first direction (e.g., x-axis) of the periodic array from a grating period $Λ_2$ in a second direction (e.g., y-axis) of the periodic array.

Referring again to FIGS. 1A and 1B, a portion of the excitation signal 102 incident on a surface of the GMR grating 110 is coupled by the grating 112 into the GMR grating 110, in various embodiments. For example, the portion of the excitation signal 102 may be coupled into the dielectric slab waveguide 114, in some embodiments. The portion of the excitation signal 102 that is coupled into the GMR grating 110 is referred to as a 'GMR-coupled portion'. Coupling occurs most prominently when a wavelength of the excitation signal 102 coincides with a guided-mode resonant frequency for a particular incident angle θ. A direction of propagation of the GMR-coupled portion of the excitation signal 102 within the GMR grating 110 is determined, in part, by the angle of incidence θ of the excitation signal 102 relative to the GMR grating 110 surface. In some embodiments, the propagation direction is further determined by a polarization (e.g., TE or TM) of the excitation signal 102.

In particular, when the excitation signal 102 has a generally TE polarization, the propagation direction of the GMR-coupled portion is in a direction determined by a vector component of the excitation signal 102 that is parallel with a surface of the GMR grating 110. For example, the exemplary excitation signal 102 illustrated in FIG. 1A has a TE polarization and includes propagation or wave vector k components in an x-direction and a y-direction. For TE polarization, an E-field component of the excitation signal 102 incident on the GMR grating 110 surface is oriented in the z-direction parallel with the GMR grating 110 surface, as illustrated. As a result, the GMR-coupled portion of the exemplary TE polarized excitation signal 102 propagates in the x-direction (i.e., to the right as illustrated by an arrow 102a) within the GMR grating 110 (e.g., within the dielectric slab waveguide 114). By convention and herein, an E-field component of an optical signal (e.g., the excitation signal 102) is illustrated by an arrow labeled 'E' while an H-field component is depicted as an arrow labeled 'H'.

In other embodiments when the excitation signal 102 has a generally transverse magnetic (TM) polarization relative to the GMR grating 110 surface, the propagation direction of the GMR-coupled portion of the exemplary TM polarized excitation signal 102 is generally orthogonal to a direction of the excitation signal 102 wave vector components at the surface of the GMR grating 110. For example, the exemplary excitation signal 102 illustrated in FIG. 1B has a TM polarization with an H-field component oriented in the z-direction parallel to the GMR grating 110 surface. The GRM-coupled portion of the exemplary excitation signal 102 propagates in a z-direction, as illustrated in FIG. 1B (i.e., in a direction indicated by arrows 102b).

The spectroscopy apparatus 100 illustrated in FIGS. 1A and 1B further comprises an optical detector 120. The optical detector 120 is configured to receive a portion of the scattered signal 106 from an analyte 104 associated with a surface of the GMR grating 110. In particular, a propagation direction of the received portion of the scattered signal 106 within the dielectric slab waveguide 114 of the GMR-grating 110 is substantially different from a propagation direction 102a, 102b of the GMR-coupled portion of the excitation signal 102 within the GMR grating 110. The substantially different propagation directions of the received portion of the scattered signal 106 and the GMR-coupled portion of the excitation signal 102 may facilitate detection of the scattered signal 106 through spatial filtering, for example.

In various embodiments, the optical detector 120 may comprise substantially any means for collecting and detection photons associated with the scattered signal 106. For example, the optical detector 120 may comprise one or more of a photodiode, photoresistor and a phototransistor. In other examples, the optical detector 120 may comprise a charge-coupled device (CCD) detector. In yet other examples, the optical detector 120 may comprise a photomultiplier tube or similar phototube devices.

According to some embodiments, the optical detector 120 is coupled to an edge of the GMR grating 110. For example, the optical detector 120 may be connected to an edge of the dielectric slab waveguide 114 to detect the GMR-coupled portion of the excitation signal 102 propagating therewithin. In another example, the optical detector 120 is coupled to an edge of the grating 112 to detect the GMR-coupled portion of the excitation signal 102 as a surface wave propagating along the GMR grating 110 surface. The edge to which the optical detector 120 is coupled is an edge of the GMR grating 110 in a direction that facilitates spatial filtering provided by the different propagation directions, according to some embodiments. In particular, the edge to which the optical detector 120 is coupled may be defined by a location of the optical detector 120 relative to the angle of incidence θ of the excitation signal 102, according to some embodiments.

For example, as illustrated in FIG. 1A for an exemplary TE polarized excitation signal 102, the optical detector 120 may be located at an end of the GMR grating 110 opposite an end of the GMR grating 110 that is in the propagation direction of the GMR-coupled portion 102a of the excitation signal 102. In other words, the optical detector 120 is located at an edge in a negative x-direction when the GMR-coupled portion propagation direction is in a positive x-direction (e.g., as illustrated). Since the GMR-coupled portion 102a of the excitation signal 102 is traveling away from the optical detector 120, the GMR-coupled portion will generally not interfere with detection of the scattering signal 106 traveling in the direction (e.g., a negative x-direction) toward the optical detector 120. The differential propagation directions providing as they do spatial filtering may obviate a need for other filtering in some embodiments, for example.

In another example and for the exemplary TM polarized excitation signal 102 as illustrated in FIG. 1B, the optical detector 120 may be located in a direction that is substantially perpendicular to the propagation direction of the GMR-coupled portion 102b of the excitation signal 102 within the GMR grating (e.g., within the dielectric slab waveguide 114 or along a surface of the GMR grating 110). In particular, the optical detector 120 may be located at an edge of the GMR grating 110 that is in the substantially perpendicular direction. For example, the optical detector 120 may be located at an edge in either the positive or negative x-directions when the GMR-coupled portion 102b of the excitation signal 102 propagates in the z-direction, as illustrated in FIG. 1B. The optical detector 120 is illustrated located at and coupled to an edge in the positive x-direction in FIG. 1B, for example.

In some embodiments, the scattering spectroscopy apparatus 100 further comprises a mirror 130, as is further illustrated in FIG. 1B. The mirror 130 functions to reflect a signal incident on the mirror 130 from the GMR grating 110 back into the GMR grating 110. For example, the mirror 130 may reflect a signal propagating in the dielectric slab waveguide 114 such that the signal propagates in an opposite direction within the dielectric slab waveguide 114 after encountering the mirror 130. In various embodiments, the mirror 130 may comprise substantially any structure or combination of structures that provide optical reflection in a range of wavelengths that includes a wavelength of the scattered signal 106 including, but not limited to, a Bragg mirror and a reflective metalized surface.

In some embodiments, the mirror 130 is located at an edge of the GMR grating 110. In particular, in some embodiments, the mirror 120 is located at a second end of the GMR grating 110 and the optical detector 120 is located at a first end of the GMR grating that is opposite the second end. In some of these embodiments, the first and second ends are located in a direction that is substantially orthogonal to the propagation direction of the GRM-coupled portion of the excitation signal 102. For example, as illustrated in FIG. 1B, the optical detector 120 and mirror 130 are located at opposite ends of the dielectric slab waveguide 114 of the GMR grating 110 in the x-direction while the GMR-coupled portion 102b of the excitation signal 102 propagates in the z-direction, as indicated by the arrows 102b.

In some embodiments, the GMR grating surface is coated with a Raman active material 140, as is further illustrated in FIG. 1A. For example, the Raman active material 140 may comprise a plurality of nanoparticles. The nanoparticles may comprise a metal such as, but not limited to gold, silver or copper and other metals with optical-range plasma frequencies (e.g., various noble metals), for example. In some embodiments, the Raman active material 140 comprises nanoantennas configured to enhance Raman scattering. For example, nanoantennas may include, but are not limited to, coupled nanospheres, thin nanoscale metal strip dipoles in pairs or end-to-end coupled arrays, nanoscale bow-tie structures, and various nanoscale metal-oxide-metal structures.

For example, a nanoantenna may comprise a pair of thin nanoscale metal strips about 50 nm in length, 20 nm in width and 10-20 nm in thickness. The pairs of thin nanoscale metal strips may be spaced apart from one another by a gap having a width of about 0-10 nm, for example. According to some embodiments, the nanoantennas may be excited by the GMR-coupled portion of the excitation signal 102. In turn, the nanoantennas and analyte may produce what amounts to a 'radiating complex' which may exhibit higher levels of Raman signal emission than would occur absent the nanoantennas.

Figure 4:
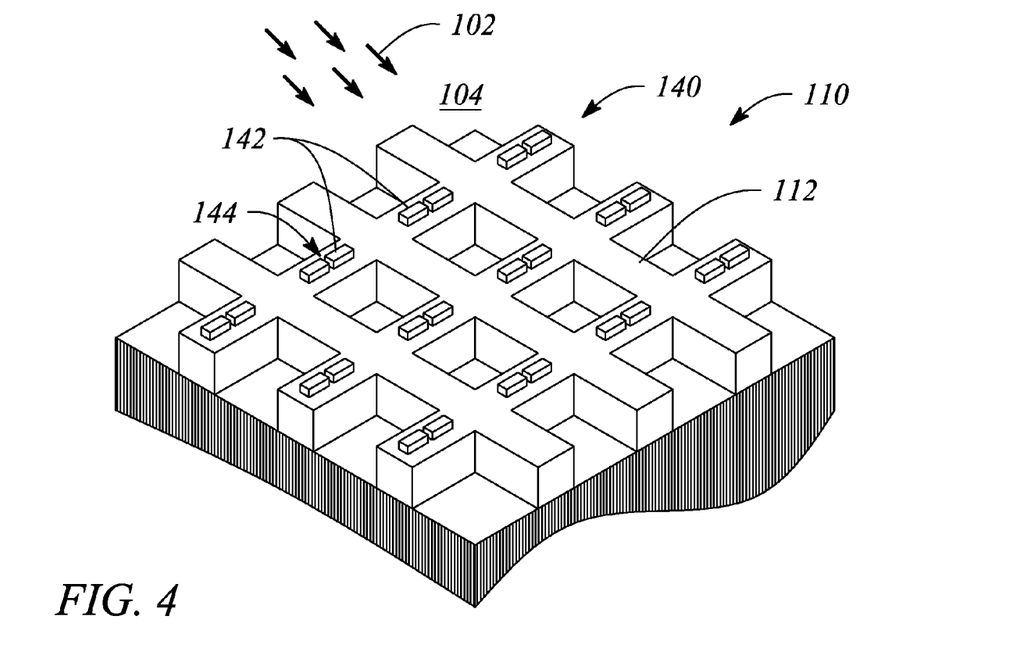
FIG. 4 illustrates a perspective view of a portion of a top surface of a GMR grating, according to an embodiment of the present invention.

FIG. 4 illustrates a perspective view of a portion of a top surface of a GMR grating 110, according to an embodiment of the present invention. As illustrated, the grating 112 of the GMR grating 110 comprises a square lattice of dielectric bars with square cavities between the bars. Further illustrated is the Raman active material 140 comprising nanoantennas 142. A field created by the GMR-coupled portion of the excitation signal 102 may be further enhanced by the nanoantennas 142, as mentioned above. In particular, extremely high field magnitudes may exist in the gap 144 between adjacent ends of the strips that make up the nanoantennas 142. In some embodiments, analytes 104 that enter or at least are in a vicinity of the gap 144 will experience the extremely high field magnitude and may produce, in conjunction with the nanoantennas 142 (e.g., as the radiating complex) enhanced levels of Raman signals, as a result. In other words, the combination of the nanoantenna 142 and analyte 104 may create an antenna-analyte complex.

Figure 5:
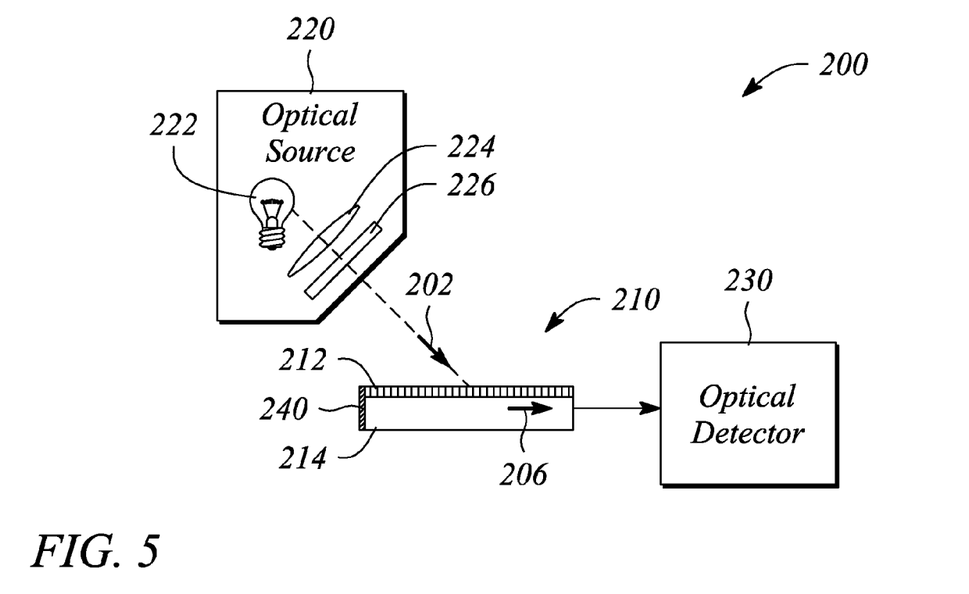
FIG. 5 illustrates a block diagram of a spectroscopy system, according to an embodiment of the present invention.

FIG. 5 illustrates a block diagram of a spectroscopy system 200, according to an embodiment of the present invention. In operation, the spectroscopy system 200 employs an interaction between an electromagnetic field provided by a portion of an optical excitation signal 202 and an analyte (not illustrated) to produce a scattered signal 206. The scattered signal 206 is indicative of the analyte to facilitate characterization thereof. For example, the scattered signal 206 may include, but is not limited to, a Raman signal and a fluorescence signal. The scattering spectroscopy system 200 thus may provide one or more of surface enhanced Raman spectroscopy (SERS) and fluorescence spectroscopy of the analyte, for example.

As illustrated in FIG. 5, the scattering spectroscopy system 200 comprises a guided-mode resonance (GMR) grating 210. The GMR grating 210 comprises a subwavelength grating 212 and a dielectric slab waveguide 214, according to some embodiments. The subwavelength grating 212 couples a portion of the optical excitation signal 202 into the GMR grating 210 as a GMR-coupled portion. For example, the subwavelength grating 212 may couple the GMR-coupled portion into the dielectric slab waveguide 214. In another example, the grating 212 may couple the GMR-coupled portion into a surface wave propagating along the subwavelength grating 212.

According to various embodiments, the GMR-coupled portion of the optical excitation signal 202 may exhibit an enhanced electromagnetic field intensity in a vicinity of the surface of the GMR grating 210 compared to an electromagnetic field intensity of the optical excitation signal 202. In particular, the GMR-coupled portion may propagate, in part, as a surface wave or surface polariton along the surface of the GMR grating 210. The surface wave may provide the enhanced field intensity. The enhanced field intensity, in turn, may facilitate or enhance generation of the scattered signal 206 from the analyte through the interaction at the GRM grating 210 surface. In some embodiments, the GMR grating 210 is substantially similar to the GMR grating 110 described above with respect to the scattering spectroscopy apparatus 100.

The scattering spectroscopy system 200 further comprises an excitation source 220. The excitation source 220 is configured to provide the optical excitation signal 202. The provided optical excitation signal 202 has an oblique angle of incidence at a surface of the GMR grating 210. In various embodiments, the excitation source 220 comprises substantially any means 222 for generating an optical signal such as, but not limited to, a laser, for example. In some embodiments, the optical excitation signal 202 may be provided as a substantially collimated and polarized optical signal. In particular, in some embodiments, the optical excitation signal 202 provided by the excitation source 220 has a transverse electric (TE) polarization relative to the GMR grating 210 surface. In some other embodiments, the optical excitation signal 202 has a transverse magnetic (TM) polarization relative to the GMR grating 210 surface. For example, the excitation source 220 may further comprise one or both of a collimating lens 224 and a polarizer 226, in some embodiments.

The scattering spectroscopy system 200 further comprises an optical detector 230. The optical detector 230 is configured to receive a portion of the scattered signal 206 from the GMR grating 210. A propagation direction within the GMR grating 210 of the received portion of the scattered signal 206 is substantially different from a propagation direction of the GMR-coupled portion of the optical excitation signal 202 within the GRM grating 210. In some embodiments, the optical detector 230 may be substantially similar to the optical detector 120 described above with respect to the scattering spectroscopy apparatus 100.

In some embodiments in which the optical excitation signal 202 has a TE polarization, the optical detector 230 is located at an end of the GMR grating 210 opposite to an end of the GMR grating 210 in the propagation direction of the GMR-coupled portion of the optical excitation signal 202. In other words, the optical detector 230 is configured to receive a portion of the scattered signal 206 (i.e., the received portion) that propagates in a direction within the GMR-grating 210 that is opposite a direction in which the GMR-coupled portion of the optical excitation signal 202 is propagating.

In some other embodiments in which the optical excitation signal 202 has a TM polarization, the optical detector 230 is located at an end of the GMR grating that is orthogonal to the propagation direction of the GMR-coupled portion of the optical excitation signal 202. In some of these other embodiments, the scattering spectroscopy system 200 further comprises a mirror 240. The mirror 240 is located at an end of the GMR grating 210 opposite to the end at which the optical detector 230 is located, according to some embodiments. In some embodiments, the mirror 240 may be substantially similar to the mirror 130 described above with respect to the scattering spectroscopy apparatus 100.

In some embodiments, the GMR grating surface is coated with a Raman active material (not illustrated). For example, the Raman active material may comprise a plurality of nanoparticles comprising a metal such as, but not limited to gold, silver or copper and other metals with optical-range plasma frequencies (e.g., various noble metals). In some embodiments, the Raman active material comprises nanoantennas configured to enhance Raman scattering. For example, nanoantennas may include, but are not limited to, coupled nanospheres, thin nanoscale metal strip dipoles in pairs or end-to-end coupled arrays, nanoscale bow-tie structures, and various nanoscale metal-oxide-metal structures. In some embodiments, the Raman active material may be substantially similar to the Raman active materials described above with respect to the scattering spectroscopy apparatus 100.

Figure 6:
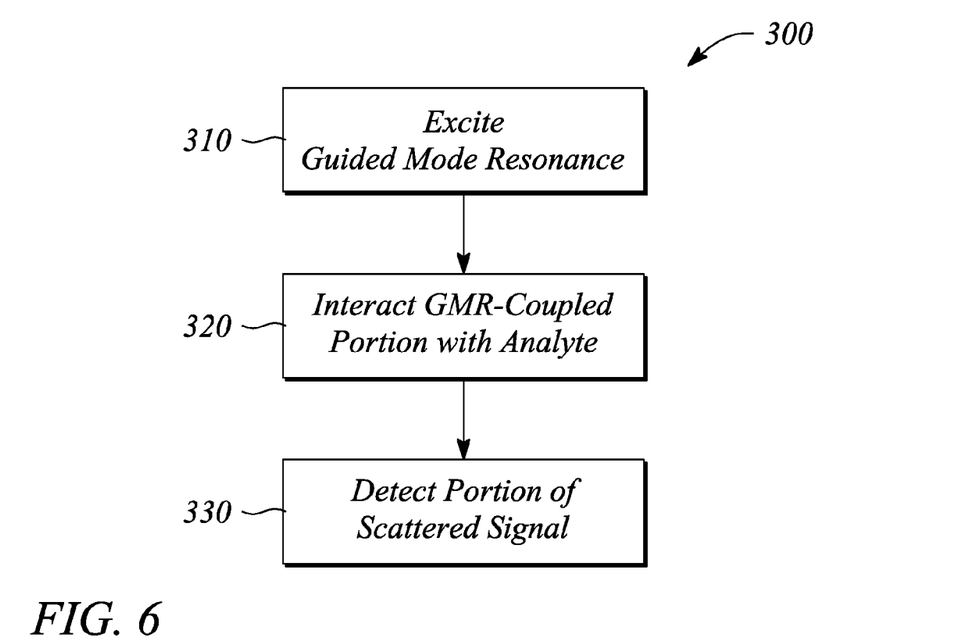
FIG. 6 illustrates a flow chart of a method of scattering spectroscopy, according to an embodiment of the present invention.

FIG. 6 illustrates a flow chart of a method 300 of scattering spectroscopy, according to an embodiment of the present invention. The method 300 of scattering spectroscopy comprises exciting 310 a guided-mode resonance (GMR) in a GMR grating by coupling a portion of an excitation signal into the GMR grating using a grating of the GMR grating. In some embodiments, the GMR grating comprises a subwavelength grating and dielectric slab waveguide and is substantially similar to the GMR grating 110 described above with reference to the scattering spectroscopy apparatus 100. The coupled portion of the excitation signal is referred to as the GMR-coupled portion and is substantially similar to the GMR-coupled portion described above with respect to the scattering spectroscopy apparatus 100, according to some embodiments.

The method 300 of scattering spectroscopy further comprises interacting 320 the GMR-coupled portion of the excitation signal with an analyte associated with a surface of the GMR grating. Interacting 320 the GMR-coupled portion produces a scattered signal. The produced scattered signal may be substantially similar to the scattered signal 106 described above with respect to the scattering spectroscopy apparatus 100, in some embodiments. In particular, according to some embodiments, the scattered signal may comprise a signal resulting from one or more of Raman scattering and fluorescence scattering by the analyte.

The method 300 of scattering spectroscopy further comprises detecting 330 a portion of the scattered signal. The portion of the scattered signal that is detected 330 is a portion propagating within the GMR grating in a direction that is substantially different from a propagation direction of the GMR-coupled portion of the excitation signal within the GMR grating, according to some embodiments. For example, detecting 330 a portion of the scattered signal may be performed by an optical detector. The optical detector may be substantially similar to the optical detector 120 described above with respect to the scattering spectroscopy apparatus 100, for example. In particular, in some embodiments in which the excitation signal comprises an optical signal having a transverse magnetic (TM) polarization relative to the surface of the GMR grating, the detected 330 portion of the scattered signal propagates in a direction that is substantially orthogonal to the propagation direction of the GMR-coupled portion of the excitation signal.

In some embodiments (not illustrated), the method 300 of scattering spectroscopy further comprises reflecting a portion of the scattered signal propagating in a first direction within the GMR grating (e.g., within the dielectric slab waveguide). After reflecting a portion of the scattered signal, the reflected scattered signal portion propagates in a second direction in which the detected portion of the scattered signal propagates. The reflected scattered signal portion combines with the detected scattered signal portion to enhance detection 330 of the scattered signal portion.

Thus, there have been described embodiments of a scattering spectroscopy apparatus and system as well as a method of scattering spectroscopy that employ a GMR grating. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. A scattering spectroscopy apparatus comprising:
    a guided-mode resonance (GMR) grating having a subwavelength grating; and
    an optical detector located at a first end of the GMR grating to receive a portion of a scattered signal from an analyte associated with a surface of the GMR grating, the received portion of the scattered signal to propagate substantially within the GMR grating in a propagation direction that is substantially different from a propagation direction of a GMR-coupled portion of an excitation signal within the GMR grating,
    wherein the scattered signal is a product of an interaction between the analyte and the excitation signal, the excitation signal having an oblique angle of incidence on the GMR grating.

2. The scattering spectroscopy apparatus of claim 1, wherein the subwavelength grating comprises a one-dimensional (1-D) grating.

3. The scattering spectroscopy apparatus of claim 2, wherein the 1-D grating comprises a 1-D surface profile of surface features formed one or both of into a surface and onto the surface of a dielectric slab waveguide of the GMR grating.

4. The scattering spectroscopy apparatus of claim 3, wherein the surface features protrude from the surface of the dielectric slab waveguide.

5. The scattering spectroscopy apparatus of claim 2, wherein the 1-D grating comprises a periodic array of dielectric features.

6. The scattering spectroscopy apparatus of claim 1, wherein the GMR grating comprises a two-dimensional (2-D) grating having a two-dimensional periodic array of grating elements, the grating elements being one or both of dielectric features and surface features.

7. The scattering spectroscopy apparatus of claim 1, wherein the excitation signal comprises an optical signal having a transverse electric (TE) polarization relative to the GMR grating surface, and wherein the first end is an end of the GMR grating opposite an end of the GMR grating that is in the propagation direction of the GMR-coupled portion of the excitation signal.

8. The scattering spectroscopy apparatus of claim 1, wherein the excitation signal comprises an optical signal having a transverse magnetic (TM) polarization relative to the GMR grating surface, and wherein the first end is an end of the GMR grating that is in a direction substantially perpendicular to the propagation direction of the GMR-coupled portion of the excitation signal.

9. The scattering spectroscopy apparatus of claim 8, further comprising a mirror at a second end of the GMR grating, the second end being opposite the first end of the GMR grating.

10. A scattering spectroscopy system comprising the scattering spectroscopy apparatus of claim 1, the system further comprises an excitation source configured to provide the excitation signal, wherein the scattered signal comprises a Raman scattering signal from the analyte.

11. A scattering spectroscopy system comprising:
    a guided-mode resonance (GMR) grating comprising a subwavelength grating and a dielectric slab waveguide;
    an excitation source configured to provide an optical excitation signal having an oblique incidence angle at a surface of the GMR grating; and
    an optical detector located at a first end of the GMR grating to receive a portion of a scattered signal from the GMR grating, the received portion of the scattered signal to propagate substantially within the GMR grating in a propagation direction that is substantially different from a propagation direction of a GMR-coupled portion of the optical excitation signal within the GMR grating,
    wherein the scattered signal comprises a signal produced by an interaction between an analyte and an electromagnetic field of the GMR-coupled portion of the optical excitation signal at the GMR grating surface.

12. The scattering spectroscopy system of claim 11, wherein the optical excitation signal has a transverse electric (TE) polarization relative to the GMR grating surface, the first end being an end of the GMR grating opposite an end of the GMR grating that is in the propagation direction of the GMR-coupled portion of the optical excitation signal.

13. The scattering spectroscopy system of claim 11, wherein the optical excitation signal has a transverse magnetic (TM) polarization relative to the GMR grating surface, the first end being an end of the GMR grating that is orthogonal to the propagation direction of the GMR-coupled portion of the optical excitation signal.

14. The scattering spectroscopy system of claim 13, further comprising a mirror at a second end of the GMR grating opposite to the first end of the GMR grating.

15. The scattering spectroscopy system of claim 11, wherein the subwavelength grating comprises a one-dimensional diffraction grating formed by a periodic array of features, the features being formed one or both of in and on a surface of the dielectric slab waveguide and comprising one or both of dielectric features and surface features.

16. The scattering spectroscopy system of claim 11, wherein the scattered signal comprises a Raman scattering signal from the analyte, and wherein the surface of the GMR grating is coated with a plurality of nanoantennas configured to enhance Raman scattering.

17. A method of scattering spectroscopy, the method comprising:
exciting a guided-mode resonance (GMR) in a GMR grating by coupling a portion of an excitation signal into the GMR grating using a grating of the GMR grating, the coupled portion being a GMR-coupled portion of the excitation signal;
interacting the GMR-coupled portion of the excitation signal with an analyte associated with a surface of the GMR grating, the interaction producing a scattered signal; and
detecting a portion of the scattered signal using an optical detector located at a first end of the GMR grating, the detected portion of the scattered signal propagating within the GMR grating in a direction that is substantially different from a propagation direction of the GMR-coupled portion of the excitation signal within the GMR grating.

18. The method of scattering spectroscopy of claim 17, wherein the excitation signal comprises an optical signal having a transverse magnetic (TM) polarization relative to the surface of the GMR grating, the detected portion of the scattered signal propagating being in a direction that is substantially orthogonal to the propagation direction of the GMR-coupled portion of the excitation signal, the first end being an end of the GMR grating that is in the substantially orthogonal propagation direction.

19. The method of scattering spectroscopy of claim 17, further comprising:
reflecting a portion of the scattered signal propagating in a first direction within the GMR grating, the reflected scattered signal portion propagating in a second direction in which the detected portion of the scattered signal propagates, wherein the reflected scattered signal portion combines with the detected scattered signal portion to enhance detection of the scattered signal.

20. The method of scattering spectroscopy of claim 17, wherein the scattered signal comprises a signal resulting from Raman scattering by the analyte.

* * * * *